US005633006A

United States Patent [19]
Catania et al.

[11] Patent Number: 5,633,006
[45] Date of Patent: May 27, 1997

[54] TASTE-MASKING COMPOSITION OF BITTER PHARMACEUTICAL AGENTS

[75] Inventors: Joseph S. Catania, Gales Ferry; Alton D. Johnson, Groton, both of Conn.

[73] Assignee: Pfizer Inc., New York, N.Y.

[21] Appl. No.: 328,977

[22] Filed: Oct. 24, 1994

Related U.S. Application Data

[63] Continuation of Ser. No. 922,262, Jul. 30, 1992, abandoned.

[51] Int. Cl.$^6$ .................... A61K 9/20; A61K 47/02
[52] U.S. Cl. ................ 424/441; 424/439; 514/974
[58] Field of Search .................... 424/499, 501, 424/439, 441, 469, 470, 688, 692; 514/974

[56] References Cited

U.S. PATENT DOCUMENTS

| | | | |
|---|---|---|---|
| 3,627,885 | 12/1971 | Rondelet et al. | 514/6 |
| 4,474,768 | 10/1984 | Bright | 514/29 |
| 4,517,359 | 5/1985 | Kobrehel et al. | 536/7.4 |
| 4,678,661 | 7/1987 | Gergely et al. | 424/466 |
| 4,761,274 | 8/1988 | Denick, Jr. et al. | 424/440 |
| 4,800,087 | 1/1989 | Mehta | 424/480 |

FOREIGN PATENT DOCUMENTS

| | | |
|---|---|---|
| 0307128 | 3/1989 | European Pat. Off. |
| 0445743 | 9/1991 | European Pat. Off. |
| 0511800 | 11/1992 | European Pat. Off. |
| 05255120 | 10/1993 | Japan . |
| WO9312771 | 7/1993 | WIPO . |

OTHER PUBLICATIONS

Chemical Abstracts, 113, No. 22, 197995j.
Chemical Abstracts, 119, No. 14, 146641g.

*Primary Examiner*—Edward J. Webman
*Attorney, Agent, or Firm*—Peter C. Richardson; Gregg C. Benson; Robert T. Ronau

[57] ABSTRACT

A pharmaceutical composition having reduced bitterness consisting of a bitter pharmaceutical agent, a taste-masking component and a pharmaceutically acceptable carrier. The taste-masking component is an alkaline earth oxide, an alkaline earth hydroxide or an alkaline hydroxide and does not interfere with the activity of the pharmaceutical agent.

17 Claims, No Drawings

TASTE-MASKING COMPOSITION OF BITTER PHARMACEUTICAL AGENTS

This is a continuation of application Ser. No. 07/922,262, filed on 30 Jul. 1992, entitled "Tastemasking Composition of Bitter Pharmaceutical Agents." (now abandoned)

BACKGROUND OF THE INVENTION

This invention relates to new and valuable taste-masking compositions wherein the bitter taste and/or aftertaste of a bitter pharmaceutical agent is reduced. This invention further relates to taste-masked pharmaceutical compositions containing a bitter pharmaceutical agent, said compositions being capable of being chewed or imbibed without the production of a bitter taste or aftertaste.

A wide variety of active pharmaceutical agents exhibit the undesirable characteristic of bitter taste production either during or immediately after oral administration. Among these are included such diverse medicinal agents as acetaminophen, ampicillin, azithromycin, chlorpheniramine, cimetidine, dextromethorphan, diphenhydramine, erythromycin, ibuprofen, penicillin, phenylbutazone, psuedoephedrine, ranitidine, spironolactone and theophylline. The azalide and erythrolide antibiotics are two particularly bitter tasting classes of pharmaceutical agents, and the azalide azithromycin is among the most bitter pharmaceutical agents known.

The bitter flavor of a bitter pharmaceutical agent in a liquid suspension is inevitably detected during the drinking process or immediately after swallowing. Additionally, the bitter flavor of a bitter pharmaceutical agent in a tablet, capsule, suspension or other oral dosage form may be detected upon administration if the bittering agent is brought into contact with the taste buds as by overlong holding of the dosage form in the mouth, by inadvertent chewing of the dosage form or by some other release of the bitter pharmaceutical agent.

The administration of an oral dosage form is generally the preferred route of administration of many of the pharmaceutical agents recited hereinabove because it provides for easy, low-cost administration. However, patient compliance can sometimes be a factor when a patient is requested to swallow a tablet, capsule or suspension. Patients give many reasons for their refusal or inability to accept the oral administration of a medicinal such as unattractive presentation, overlarge size, bad taste or simple fear that an unchewed dosage form may catch in the throat. Patients who have difficulties with oral dosage forms often exhibit a gag reflex which effectively prevents oral administration. This problem is common in, but not specific to, children.

It is therefore desirable to formulate pharmaceutical agents in such a way that the above-mentioned problems are overcome. Thus, chewable tablets have been developed which have been shown to increase patient compliance in both children and others who have a problem swallowing whole tablets or capsules. However, quite often a pharmaceutical agent is so bitter-tasting that it cannot be tolerated when chewed, and the unpleasant taste or aftertaste imparted by the bittering agent will serve to disincline patients from self-administering the oral dosage form. There is, therefore, a need to mask the taste of bitter pharmaceutical agents such that the bitter flavor is reduced or eradicated from any oral dosage form which may be required for administration.

Conventionally, sweeteners and flavorants have been used in taste-masking. These agents generally work by providing a secondary flavor to the composition which it is hoped will overwhelm any bitter flavor. This technique is sometimes able to mask mildly bitter pharmaceuticals, but the traditional sweeteners are not effective in masking the bitter flavor of powerfully bitter pharmaceutical agents such as azithromycin.

Alternative approaches which have been used to mask the bitter flavor of certain pharmaceuticals include microencapsulating the unpleasant tasting active agent in a coating of ethyl cellulose or a mixture of ethyl cellulose and hydroxypropyl cellulose or other cellulose derivatives to provide chewable taste-masked dosage forms. These prior art products, however, suffer from the disadvantage that the polymer coating releases the active agent in an inconsistent fashion and may not provide immediate (or timely) release. Further, the use of said cellulose derivatives in and of themselves is quite often insufficient to provide adequate taste-masking of potently bitter active agents such as azithromycin.

Azithromycin is the generic (United States Adopted Names) name for 9-deoxo-a-aza-9a-methyl-9a-homoerythromycin A, a broad spectrum antibiotic which has one of the most potently bitter flavors known. Azithromycin is disclosed by Kobrehel et al., U.S. Pat. No. 4,517,539, the disclosure of which is hereby incorporated by reference. Azithromycin is also known as N-methyl-11-aza-10-deoxo-10-dihydroerythromycin.

The aforementioned bitter taste of azithromycin poses a serious patient compliance problem unless formulated in an oral dosage form in which said bitter taste is masked or reduced. Currently, azithromycin is being marketed as a non-chewable capsule. This presents a problem for some patients, as indicated hereinabove.

It is therefore an object of this invention to provide a method of reducing the bitterness of bitter pharmaceutical agents.

It is a further object of this invention to provide an orally administrable liquid and a chewable, taste-masked formulation of various bitter pharmaceutical agents.

It is a still further object of this invention to provide a chewable, taste-masked formulation of azithromycin which does not exhibit the bitter, unpleasant taste characteristic of azithromycin.

SUMMARY OF THE INVENTION

The present invention is directed to a pharmaceutical composition having reduced bitterness comprising a bitter pharmaceutical agent; a basic compound selected from the group consisting of alkaline earth oxides and alkaline earth hydroxides; and a pharmaceutically acceptable carrier or diluent.

A preferred group of compositions of this invention comprises the compositions recited hereinabove wherein the basic compound is an alkaline earth oxide and the bitter pharmaceutical agent is an azalide.

A further preferred group of compounds of this invention comprises the preferred compositions recited hereinabove wherein the alkaline earth oxide is magnesium oxide.

Especially preferred within the latter group are the compositions of this invention wherein the azalide is azithromycin or a pharmaceutically acceptable salt thereof.

Advantageously, the pharmaceutical composition of this invention further comprises an aldonic acid or a pharmaceutically acceptable salt thereof. A preferred aldonic acid for use in this invention is gluconic acid and an especially preferred embodiment utilizes calcium gluconate.

This invention further embraces a method of reducing the bitterness of a bitter pharmaceutical comprising formulating said bitter pharmaceutical agent as a pharmaceutical composition as recited hereinabove.

This invention still further embraces a method of treating bacterial infections in a mammal suffering from a bacterial infection comprising administering to said mammal an antibacterial effective amount of a pharmaceutical composition as recited hereinabove.

The taste-masked formulations of this invention are capable of being administered either as chewable tablets or as a liquid suspension. In either case, the present compositions provide the substantial benefit that the bitter taste and aftertaste of bitter pharmaceutical agents, particularly azithromycin, is effectively masked such that the patient does not detect the bitter flavor. Further, the taste-masking component of the present invention does not adversely alter intended medicinal effect(s) of the pharmaceutical agent of the composition.

DETAILED DESCRIPTION OF THE INVENTION

The present invention is directed to pharmaceutical compositions having reduced bitterness comprising a bitter pharmaceutical agent, a taste-masking component and a pharmaceutically acceptable carrier or diluent. The taste-masking component may consist of said basic compound as recited hereinabove alone or in combination with an aldonic acid or a pharmaceutically acceptable salt of an aldonio acid. It is generally preferred that the taste-masking component is a combination of said basic compound and a pharmaceutically acceptable salt of an aldohic acid.

To prepare the pharmaceutical composition of the present invention is a straightforward procedure. The desired pharmaceutical agent is mixed with the taste-masking component and blended well. More specifically, the pharmaceutical agent is mixed with said basic compound selected from the group consisting of alkaline earth oxides and alkaline earth hydroxides. Occasionally it will be desirable to further enhance the taste-masking effects of the composition by the addition of an aldonic acid or a pharmaceutically acceptable salt thereof.

The amount of pharmaceutical agent used will vary depending upon the dosage requirements of the particular pharmaceutical agent being utilized. Generally the amount of said pharmaceutical agent will range from about 10% of the total weight of the composition to about 90% of the total weight of the composition and preferably from about 10% to about 50%. The amount of said basic compound will vary according to the amount of bitter pharmaceutical agent utilized and the degree of bitterness of said bitter pharmaceutical agent. Generally, however, the amount of said basic compound utilized will range from about 1% of the total weight of the composition to about 25% of the total weight of the composition and preferably from about 1% to about 16%. The amount of aldonic acid (or pharmaceutically acceptable salt thereof) utilized will also depend upon the amount of the pharmaceutical agent utilized and upon the degree of bitterness of said pharmaceutical agent. Generally, the amount of aldonic acid (or pharmaceutically acceptable salt thereof) used will range from about 0% to about 25% of the total weight of the pharmaceutical composition. When used, the amount of aldonic acid (or pharmaceutically acceptable salt thereof) used will preferably be from about 5% to about 20%. Generally, the amount of basic compound required is less when used in combination with an aldonio acid (or salt thereof) and in such cases the preferred amount of said basic compound will range from about 1% to about 10%.

The pharmaceutical composition described hereinabove is sufficient to provide the taste-masking of a wide variety of bitter pharmaceutical substances, including such potently bitter substances as the azalide class of antibiotics, of which class azithromycin is a member.

Said basic compound of the present invention is an alkaline earth oxide or an alkaline earth hydroxide. Examples of suitable such basic compounds include, but are not limited to, such compounds as calcium hydroxide, magnesium oxide, calcium oxide and the like. All of said basic compounds of the present invention are readily available.

Said aldonic acids used herein are readily available derivatives of sugars such as gluconic acid, mannonic acid, galactonic acid and the like. When the aldonic acid is not readily available, said aldonic acid can be simply prepared utilizing the methods well known to one skilled in the art. Thus the readily available aldose is oxidized with either bromine in water or a weak nitric acid solution to yield the corresponding aldonic acid derivative.

The pharmaceutically acceptable salts of said aldonic acids are prepared by reacting the aldonic acid with an appropriate base, usually one equivalent, in a co-solvent. Typical bases are sodium hydroxide, sodium methoxide, sodium ethoxide, potassium methoxide, magnesium hydroxide, calcium hydroxide, benzathine, choline, diethanolamine, ethylenediamine, meglumine, benethamine, diethylamine, piperazine and tromethamine. The salt is isolated by concentration to dryness or by addition of a non-solvent. In some cases, salts can be prepared by mixing a solution of the aldonic acid with a solution of a different salt of the cation (sodium ethylhexanoate, magnesium, or calcium oleate), employing a solvent in which the desired cationic salt precipitates, or can be otherwise isolated by concentration and addition of a non-solvent. Generally, the preferred aldonic acid salts, such as calcium gluconate, are readily available.

The expression "pharmaceutically acceptable salt" is intended to define such salts as the alkali metal salts (e.g. sodium and potassium), the alkaline earth metal salts (e.g. magnesium and calcium), aluminum salts, ammonium salts and salts with organic amines such as benzathine, choline, diethanolamine, ethylenediamine, meglumine, benethomine, diethylamine, piperazine, tromethamine and the like.

The bitter pharmaceutical agents of the present invention include, but are not limited to, such bitter pharmaceutical agents as acetaminophen, ampicillin, azithromycin, chlorpheniramine, cimetidine, clarithromycin, diphenhydramine, erythromycin, ibuprofen, penicillin, phenylbutazone, ranitidine, spironolactone, theophylline and the like. All of the above-mentioned bitter pharmaceutical agents are prepared by the methods recited in the Merck Index, Tenth Edition, Merck and Co., Rahway, N.J. (1983) or by references cited therein, excepting clarithromycin and azithromycin. Azithromycin is prepared by the method recited in Bright, U.S. Pat. No. 4,474,768. Azithromycin dihydrate is prepared by the method recited in International Patent Publication No. WO89/00576. Clarithromycin is prepared by the method recited in Watanabe et al., Heterocycles, 1990, 31, 2121–4.

The composition as described above provides the desired taste-masking characteristics of the present invention. To prepare the tablet or powder form (for constitution) it is often desirable to add other excipients to the above-recited composition. These excipients may include sweeteners, flavorants, binders, stabilizers, plasticizers, pigments, bulking agents and the like.

Sweeteners are sometimes used to impart a pleasant flavor to the taste-masked composition. The sweet flavor imparted by said sweeteners is not altered or reduced by the taste-masking component. Said taste-masking component is specific for the taste-masking of bittering agents. Preferred sweeteners include artificial sweeteners such as aspartame, saccharin, cyclamates and the like, including mixtures of aspartame and saccharin. Sometimes natural sweeteners such as sucrose, fructose, glucose, sodium glycolate and the other mono- and disaccharides are preferred. Also preferred are mixtures of artificial and natural sweeteners, such as the mixture of aspartame and sucrose and other such mixtures. The sweetener comprises about 0.02% to about 75% by weight of the tablet, depending upon the sweetener used. Of course, the amount of aspartame and saccharin used will generally be much smaller than the amount of the other sweeteners mentioned above and preferably will be less than about 5% of the weight of the tablet to be administered, when used alone.

Flavorants may also be used to improve the flavor of the composition and, as with the sweeteners, the pleasant flavor of the flavorant is not altered or reduced by the taste-masking component of the present invention. The flavorants recited hereinbelow may be used singly or in combination. Preferred flavorants include, but are not limited to, cherry, strawberry, grape, cream, vanilla, chocolate, mocha, spearmint, cola and the like. In general the total amount of flavorant required to elicit satisfactory flavoring of the composition is at most 3% by weight of the pharmaceutical composition.

Binders which may be used in the preparation of tablet forms of the present invention include such binding agents as hydroxypropyl cellulose, hydroxypropyl methylcellulose, carboxymethyl methylcellulose sodium and methylcellulose. The amount of binder used will be dependent upon the nature of the particular pharmaceutical agent which is being manufactured, but generally the amount of binder will not exceed 5% of the total weight of the pharmaceutical composition.

The composition may also contain a pigment which may be used to improve the appearance of the tablet since an attractive coloration imparted by a pigment can sometimes improve patient compliance. Generally the particle size of the pigments will be between five and ten micrometers, when said pigment is used. Pigments such as titanium dioxide, iron oxide and various other color pigments, including vegetable dyes, may be used. The shelf-life of light sensitive or otherwise unstable pharmaceutical agents can often be improved by the stabilizing effects of pigments and opacifiers. When pigments or opacifiers are used, it is sometimes preferred that non-ionic plasticizers such as polysorbate 60, polysorbate 80, polyvinyl pyrolidone, propylene glycol and the like be used if the use of a plasticizer is desired.

In many embodiments of this invention it may be desirable to add a diluent or bulking agent to the composition. Acceptable diluents useful in embodiments of the present invention include dextrose, sorbitol, sucrose, lactose and mannitol, urea, salts, for example potassium chloride, sodium chloride, salts of phosphate, gelatin, starch, the natural and synthetic cellulose derivative including, for example methyl-, ethyl-, propyl-, hydroxymethyl, hydroxyethyl, hydroxypropyl or hydroxypropyl methyl cellulose, silica, polyvinyl alcohol, polyvinylpyrrolidone and stearic acid and its salts, for example, magnesium stearate, among others. Generally, the type and amount of diluent or bulking agent is dependent upon the physicochemical characteristics of the pharmaceutical agent being formulated. The diluent generally comprises from about 0.1% to about 95% by weight of the composition and preferably comprises between about 10% to about 35% by weight of the composition.

The preparation of the pharmaceutical composition can be accomplished by utilizing any one of a wide variety of different prior art methods well known to one of ordinary skill in the art. Preferably, the active pharmaceutical agent is mixed with the taste-masking component, sweeteners and other excipients and blended in a blender. The blend is added to a solution of a binder or bulking agent such as hydroxypropyl cellulose in water in a wet massing apparatus (such as a Hobart Model A200T Mixer). Generally it is preferable to add the blend to the aqueous solution in portions. Following each addition of blend, the contents are mixed thoroughly by the wet massing apparatus until a wet massing endpoint is achieved. Said wet massing endpoint is detected by visual examination, as is understood by one of ordinary skill in the art.

The wet-massed granulation obtained from the wet-massing step is dried and the dried blend is generally processed further by sizing the granulation through a mill and placing the sized granulation in a blender. At this point any flavorants which may be desired are added, with blending. Any other excipient which is desired but which has not already been added is generally added at this point.

After this final blend the composition is ready to be placed into its final dosage form. If the dosage form is simply a powder which is to be constituted into a liquid suspension by the pharmacist or other qualified person, the preparation is complete. Furthermore, the wet-massed granulation step is optional when a suspension dosage form is desired. If the final dosage form is to be a chewable tablet, the composition prepared as recited above is transferred to a tablet press (such as a Manestry F3 Tablet Press). The size of the tablet will be determined by the amount of the pharmaceutical agent which it is desired to dispense with each dosing, and will vary depending upon the potency of the individual pharmaceutical agent. Generally, for azithromycin, the size of the tablet will be from about 250 mg to about 1500 mg and the amount of active agent present in the tablet will be from about 100 mg to about 500 mg.

Administration of the formulations of the present invention is achieved according to the normal oral mode of administration, that is, the tablets are placed in the mouth, chewed and then swallowed. The tablets may be ground up and mixed with, placed in or sprinkled on cereal, ice cream or other foods or drinks and then ingested. Alternatively, the tablets may be swallowed whole, if preferred, without chewing or admixing. When a reconstitutable form of the composition is administered as a liquid suspension, said suspension is generally simply imbibed. Alternatively said suspension may be mixed with foods and drinks if preferred, as recited hereinabove for tablets.

The term azalide, when used herein, means any semi-synthetic erythromycin derivative containing a nitrogen atom as part of the ring system. (See, for example, Bright et al., *Journal of Antibiotics*, 1988, 41, 102947).

The following examples are given by way of illustration and are not to be construed as a limitation in any way of this invention, many variations of which are possible within the scope thereof.

EXAMPLE 1

Azithromycin Chewable Tablet #1

Sucrose (1433.216 g), azithromycin dihydrate (530.784 g, 13.4% of total composition), mannitol (1200 g), pregelatinized starch (200 g) and magnesium oxide (280 g, 7.0% of total composition) were placed in a blender and blended for 15 minutes. The blend was passed through a sieve and blended for another 15 minutes. To a wet massing machine's vessel was added a 10% w/w solution of hydroxypropyl cellulose (prepared by adding 40 g of hydroxypropyl cellulose to 360 g of warm (60° C.) water with stirring) and the blend was added in four equal portions with the mixer operating on slow speed. After each addition, the contents were mixed thoroughly to reach a wet granulation endpoint. The wet granulated blend was transferred to polyethylene-lined trays and dried at 50° C. The dried blend was further granulated to size by passing through a mill. The granulated blend was then transferred to a blender and blended for five minutes. To the blend was added aspartame (100 g), artificial cherry flavor (32.000 g), artificial cream flavor (32.000 g) and artificial strawberry flavor (32.000 g) and the mixture was blended for ten minutes. To the blend was added magnesium stearate (120.000 g) and the mixture was further blended for five minutes. The contents of the blender were removed from the blender and compressed using a tablet press. This procedure yielded 4000 one gram tablets, each containing 125 mg of azithromycin.

EXAMPLE 2

Azithromycin Chewable Tablet #2

Azithromycin dihydrate (1619.870 g, 60% of total composition), F.D. and C. Red #40 (1.125 g), magnesium oxide (309.757 g, 11.5% of total composition), calcium gluconate (46.4160 mg, 1.7% of total composition) and sodium starch glycolate (139.248 g) were combined in an eight quart "V" blender and blended for 30 minutes. The blend was passed through a Fitzpatrick JT Comminutor fitted with a #0 plate (0.027 inch opening) at medium speed with the hammers forward. The mixture was then returned to the blender and blended for an additional thirty minutes. The blend was transferred to an eight quart Hobart Planetary Mixer (Model C-100) and mixed at the slow (#1) setting. During mixing, the mixture was wet massed by the addition of 50 g of hydroxypropyl cellulose solution (prepared by adding 45 g of hydroxypropyl cellulose to 405 g of warm (60° C.) water with stirring). Water (108 g) was added and the mixture was mixed for ten minutes. An additional 85 g of water was added to the granulation to achieve the endpoint. The mixer was continued at the slow setting for an additional five minutes to granulate the mass. The wet mixture was transferred to a polyethylene-lined tray and heated at 50° C. in a forced air over overnight (16 hours). The dried mass was passed through a Fitzpatrick JT Comminutor fitted with a #2A plate (0.093 inch opening) at slow speed with the knives forward. The granulation was transferred to an eight quart "V" blender, flavors were added and the flavored granulation was blended for thirty minutes. Magnesium stearate (45 g) was added and the mixture was blended for five minutes. The mixture was compressed into tablets to achieve a final tablet weight of 750 mg±3%.

EXAMPLE 3

Azithromycin Suspension #1

Sucrose (1433.216 g), azithromycin dihydrate (530.784 g), mannitol (1200 g), pregelatinized starch (200 g) and magnesium oxide (280 g) were placed in a blender and blended for 15 minutes. The blend was passed through a sieve and blended for another 15 minutes. To the blend was added aspartame (100 g), artificial cherry flavor (8.000 g), artificial cream flavor (8.000 g) and artificial strawberry flavor (8.000 g) and the mixture was blended for ten minutes. To the blend was added magnesium stearate (30.000 g) and the mixture was further blended for five minutes. The contents of the blender were removed from the blender and packaged for constitution with water.

EXAMPLES 4–15

Using substantially the same procedure as recited in Example 1, but utilizing the differing amounts of azithromycin dihydrate and magnesium oxide recited (as percentages of the total composition) hereinbelow, the following examples were prepared.

| EXAMPLE | PERCENT AZITHROMYCIN | PERCENT MgO |
|---|---|---|
| 4 | 21.4 | 3.5 |
| 5 | 35.7 | 1.7 |
| 6 | 35.7 | 3.4 |
| 7 | 35.7 | 6.9 |
| 8 | 30.6 | 16.0 |
| 9 | 13.4 | 6.5 |
| 10 | 13.4 | 7.5 |
| 11 | 26.5 | 7.0 |
| 12 | 26.5 | 14.0 |
| 13 | 31.8 | 6.5 |
| 14 | 13.1 | 6.5 |
| 15 | 13.1 | 1.6 |

EXAMPLES 16–29

Using substantially the same procedure as recited in Example 2, but utilizing the differing amounts of azithromycin dihydrate, magnesium oxide and calcium gluconate recited (as percentages of the total composition) hereinbelow, the following examples were prepared.

| EXAMPLE | % AZITHROMYCIN | % MgO | % CaGLUCONATE |
|---|---|---|---|
| 16 | 21.4 | 4.1 | 11.0 |
| 17 | 13.3 | 2.5 | 13.7 |
| 18 | 13.3 | 6.5 | 7.0 |
| 19 | 13.1 | 1.5 | 16.5 |
| 20 | 31.8 | 3.1 | 16.5 |
| 21 | 31.4 | 4.6 | 16.5 |
| 22 | 31.5 | 6.2 | 16.5 |
| 23 | 59.0 | 9.5 | 6.6 |
| 24 | 59.0 | 11.5 | 23.5 |
| 25 | 71.0 | 13.8 | 9.2 |
| 26 | 71.0 | 13.8 | 8.5 |
| 27 | 71.0 | 13.8 | 5.4 |
| 28 | 71.0 | 13.8 | 7.4 |
| 29 | 72.0 | 13.8 | 6.2 |

EXAMPLES 30–34

Azithromycin Suspension

Azithromycin was mixed with magnesium oxide and the mixture was suspended in 50 mL of water to afford an oral suspension.

| EXAMPLE | AZITHROMYCIN (mg) | MgO (mg) |
|---|---|---|
| 30 | 600 | 20.65 |
| 31 | 500 | 103 |
| 32 | 500 | 51.63 |
| 33 | 500 | 25.81 |
| 34 | 500 | 12.91 |

EXAMPLES 35-39

Azithromycin, magnesium oxide and calcium gluconate were mixed and suspended in water (50 mL) to afford an orally administrable suspension.

| EXAMPLE | AZITHROMYCIN (mg) | MgO (mg) | CALCIUM GLUCONATE (mg) |
|---|---|---|---|
| 35 | 300 | 15.5 | 165.3 |
| 36 | 300 | 65 | 165.3 |
| 37 | 300 | 16 | 165.3 |
| 38 | 300 | 35 | 165.3 |
| 39 | 300 | 46.5 | 165.3 |

We claim:

1. A chewable tablet or liquid suspension pharmaceutical composition having reduced bitterness comprising azithromycin, an alkaline earth oxide and a pharmaceutically acceptable carrier.

2. A composition of claim 1 wherein said azithromycin comprises 10% to 90% of the total weight of the composition and said alkaline earth oxide comprises an amount sufficient to reduce the bitterness of said azithromycin.

3. A composition of claim 2 wherein said alkaline earth oxide comprises 1% to 16% of the total weight of the composition.

4. A composition of claim 3 wherein said alkaline earth oxide is magnesium oxide.

5. A composition of claim 4 wherein said azithromycin comprises 10% to 50% of the total weight of the composition.

6. A composition of claim 5 additionally comprising a flavorant.

7. A composition of claim 6 wherein said flavorant is selected from the group consisting of cherry, strawberry, grape, cream, vanilla, chocolate, mocha, spearmint and cola.

8. A composition of claim 7 wherein said azithromycin comprises 10% to 50% of the total weight of the composition.

9. A composition of claim 8 wherein said flavorant is grape.

10. A composition of claim 9 wherein said grape flavorant comprises not more than 3% of the total weight of the composition.

11. A composition of claim 3 additionally comprising an aldonic acid or a pharmaceutically acceptable salt thereof, said aldonic acid comprising 1% to 25% of the total weight of the composition.

12. A composition of claim 11 wherein said aldonic acid occurs as a pharmaceutically acceptable salt.

13. A composition of claim 12 wherein said pharmaceutical salt of said aldonic acid is calcium gluconate.

14. A composition of claim 13 wherein said magnesium oxide comprises 1% to 16% of the total weight of the composition.

15. A composition of claim 14 wherein said azithromycin comprises 10% to 50% of the total weight of the composition.

16. A method of reducing the bitterness of azithromycin comprising formulating said azithromycin as a pharmaceutical composition according to claim 1.

17. A method of treating a bacterial infection in a mammal suffering from a bacterial infection comprising administering to said mammal an antibacterially effective amount of a pharmaceutical composition according to claim 1.

* * * * *